United States Patent
Okuhira et al.

(10) Patent No.: US 6,794,479 B2
(45) Date of Patent: Sep. 21, 2004

(54) COMPOSITION OF POLYEPOXIDE AND OXAZOLIDINE LATENT CURING AGENT

(75) Inventors: Hiroyuki Okuhira, Kanagawa (JP); Kazunori Ishikawa, Kanagawa (JP)

(73) Assignee: The Yokohama Rubber CO, LTD, Tokyo (JP)

( * ) Notice: Subject to any disclaimer, the term of this patent is extended or adjusted under 35 U.S.C. 154(b) by 154 days.

(21) Appl. No.: 10/226,150

(22) Filed: Aug. 23, 2002

(65) Prior Publication Data

US 2003/0100676 A1 May 29, 2003

Related U.S. Application Data

(62) Division of application No. 09/758,236, filed on Jan. 12, 2001, now abandoned.

(30) Foreign Application Priority Data

Jan. 12, 2000 (JP) ........................................ 2000-003822
Jun. 21, 2000 (JP) ........................................ 2000-185777
Dec. 11, 2000 (JP) ........................................ 2000-375759

(51) Int. Cl.$^7$ ...................... C07D 261/02; C08G 59/14; C08L 63/00; C08L 63/02
(52) U.S. Cl. ...................... 528/117; 525/453; 525/504; 525/523; 548/240
(58) Field of Search ........................ 548/240; 525/453, 525/504, 523; 528/117

(56) References Cited

FOREIGN PATENT DOCUMENTS

| AT | 7501905 A | * | 8/1976 | |
| JP | 8-157563 A2 | | 6/1996 | |
| JP | 08157563 A | * | 6/1996 | ........... C08G/59/40 |
| PL | 173103 B1 | | 1/1998 | |

OTHER PUBLICATIONS

Devillers et al., Chemical abstracts accession No. 1974; 70188, "PMR study of two 1,3–oxazolidines unsubstituted in the 4 and 5 positions,", C.R. Acad. Sci., Ser. C (1973), vol. 277, No. 21, pp. 1067–1069.

Parkkinen et al., Chemical abstracts accession No. 1989–7333, "Proton NMR spectral detection of the intermediates involved in the acid–catalyzed hydrolysis of 2–substituted 3–methyl–1,3–oxazolidines," J. Chem. Soc., Perkin Trans. 2 (1988), (6), pp. 827–831.

Lehtela et al., "Mass spectrometric behavior of simple oxazolidines under electron impact and chemical ionization," Org. Mass Spectrom. (994), vol. 29, No. 11, pp. 647–653.

* cited by examiner

*Primary Examiner*—Robert Sellers
(74) *Attorney, Agent, or Firm*—Rader Fishman & Grauer

(57) ABSTRACT

A moisture-curable epoxy resin composition comprises a polyepoxide and a 2-alkyl-3-methyl or ethyl-oxazolidine wherein the 2-alkyl group the alkyl group is attached to the oxazolidine ring via a secondary or tertiary carbon atom.

4 Claims, No Drawings

COMPOSITION OF POLYEPOXIDE AND OXAZOLIDINE LATENT CURING AGENT

This is a divisional of application Ser. No. 09/758,236 filed Jan. 12, 2001, abandoned.

BACKGROUND OF THE INVENTION

This invention relates to a one-part epoxy resin composition. More specifically, this invention relates to a moisture-curable epoxy resin composition exhibiting excellent storage stability simultaneously with excellent depth curability; a novel latent curing agent which is capable of imparting a moisture-curable resin composition with sufficient storage stability together with satisfactory depth curability; a moisture-curable epoxy resin composition which exhibits excellent storage stability simultaneously with good curability, and in particular, good surface curability; a moisture-curable epoxy resin composition which has excellent surface curability and depth curability as well as excellent storage stability.

The epoxy resin compositions are most often formulated as a two-part formulation, and in use, the epoxy resin part is mixed with a curing agent and a curing accelerator to promote the curing reaction. However, it is quite troublesome to conduct the mixing immediately before use, and such mixing procedure is often associated with inaccurate measurement or erroneous mixing. In view of such situation, there is a strong demand for a one-part curable epoxy resin composition. A one-part curable epoxy resin composition known in the art is the one using dicyandiamide, imidazole, or the like for the latent curing agent. The compositions of this type, however, required the step of heating for their curing.

Latent moisture-curable curing agents which cure at room temperature are known, and ketimine compounds are typical of such agents.

Various investigations have been conducted on the one-part moisture-curable resin compositions utilizing a latent curing agent, and in particular, those utilizing the ketimine compound. The latent curing agents, however, suffered from the problem of poor storage stability and often underwent gradual viscosity increase or gelation when they were stored in sealed condition after their mixture with the epoxy resin due to high nucleophilicity of the nitrogen atom in imine moiety of the ketimine compound.

Under such circumstances, there have been disclosed various inventions where improvement in the storage stability is sought, for example, use of a ketimine compound having the imine moiety which is sterically hindered to a considerable degree as a latent curing agent which enables improved storage stability. The moisture-curable resin composition using such ketimine compound for the latent curing agent enjoyed good balance between the storage stability and the curing speed. Such composition, however, suffered from insufficient depth curability, and when such composition was used, only a very thin cured film could be formed in a short period.

On the other hand, use of an oxazolidine compound for the latent curing agent of the moisture-curable resin composition was also investigated in order to improve the depth curability of the moisture-curable resin composition. However, use of conventional oxazolidine compound resulted in an insufficient storage stability of the resulting moisture-curable resin composition despite the fairly improved depth curability.

In addition, when an oxazolidine compound is used for the latent curing agent of a one-part epoxy resin composition, the resulting composition suffered from inferior surface curability despite its acceptable depth curability and a period as long as several days was necessary for complete cure of the coated surface.

In view of the situation as described above, an object of the present invention is to solve the problems of the prior art as described above, and to provide:

(1) a moisture-curable epoxy resin composition which is a one-part epoxy resin composition having excellent storage stability simultaneously with excellent depth curability;

(2) a novel latent curing agent which is capable of imparting a moisture-curable resin composition with sufficient storage stability together with satisfactory depth curability;

(3) a one part, room temperature-curable, moisture-curable epoxy resin composition which exhibits excellent storage stability and curability;

(4) a moisture-curable epoxy resin composition which exhibits excellent storage stability simultaneously with excellent depth curability and surface curability.

The epoxy resin compositions of the present invention are not limited for their use as a one-part type, and the epoxy resin compositions may be used as a two-part type by mixing with the curing agent immediately before their use.

More illustratively, the present invention provides an oxazolidine compound represented by formula (1):

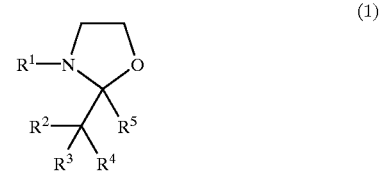

wherein
$R^1$ is methyl group or ethyl group;
$R^2$ is an alkyl group containing 1 to 6 carbon atoms;
$R^3$ is methyl group or ethyl group;
$R^4$ is hydrogen atom, methyl group or ethyl group; and
$R^5$ is hydrogen atom or a hydrocarbon group containing 1 to 6 carbon atoms;

with the proviso that $R^2$, $R^3$ and $R^4$ may together represent an alicyclic ring or an aromatic ring; and that $R^3$ and $R^5$ may together represent an alicyclic ring or an aromatic ring.

In the formula, $R^2$ is preferably methyl group.

Also provided is a moisture-curable epoxy resin composition comprising a polyepoxy compound having two or more epoxy groups on average in the molecule, and the oxazolidine compound of the present invention represented by the formula (1).

The moisture-curable epoxy resin composition may further comprise a ketimine compound synthesized from a ketone or an aldehyde represented by formula (2):

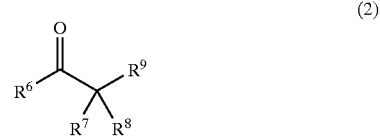

wherein $R^6$ is hydrogen atom or methyl group;

$R^7$ is an alkyl group containing 1 to 6 carbon atoms;

$R^8$ is methyl group or ethyl group; and $R^9$ is hydrogen atom, methyl group or ethyl group;

with the proviso that $R^7$, $R^8$ and $R^9$ may together represent an alicyclic ring or an aromatic ring; and that $R^6$ and $R^7$ may together represent an alicyclic ring or an aromatic ring; and a polyamine.

The backbone of the polyepoxy compound may preferably contain up to 10% by mole of hydroxyl group. It should also be construed that the case wherein no hydroxyl group is included in the backbone of the polyepoxy compound is also within the scope of the invention.

The present invention also provides a latent curing agent containing the oxazolidine compound of the present invention represented by the formula (1), or containing the oxazolidine compound and the ketimine compound as described above.

The present invention also provides a moisture-curable epoxy resin composition comprising a polyepoxy compound having at least two epoxy groups on average in the molecule; an oxazolidine compound and/or ketimine compound; and a silyl phosphate ester and/or acidic phosphoric acid.

The present invention also provides a moisture-curable epoxy resin composition comprising a polyepoxy compound having at least two epoxy groups in the molecule; and an oxazolidine compound represented by formula (16):

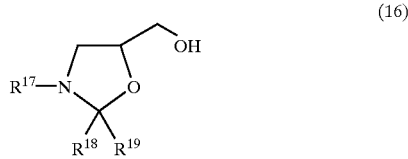

(16)

wherein $R^{17}$ is a hydrocarbon group containing 1 to 6 carbon atoms; and $R^{18}$ and $R^{19}$ either independently represent hydrogen atom or a hydrocarbon group containing 1 to 15 carbon atoms, or together represent an alicyclic ring or an aromatic ring.

$R^{17}$ is preferably methyl group or ethyl group.

The first positioned carbon atom of $R^{18}$ is preferably a branched carbon or a ring member carbon.

The present invention also provides a moisture-curable epoxy resin composition further comprising a ketimine compound.

The carbon atom and/or the nitrogen atom in the ketimine bond (C=N) of the ketimine compound may preferably have tertiary or quaternary carbon at its α position.

PREFERRED EMBODIMENTS OF THE INVENTION

Next, the present invention is described in further detail.

The present invention is directed to an oxazolidine compound, and a variety of moisture-curable epoxy resin compositions which contain an oxazolidine compound as their latent curing agent for the polyepoxy compound. Included in the present invention are the first to fifth aspects of the invention as described below.

First aspect: an oxazolidine compound represented by the formula (1).

Second aspect: a moisture-curable epoxy resin composition comprising a polyepoxy compound and an oxazolidine compound represented by the formula (1).

Third aspect: a latent curing agent comprising an oxazolidine compound represented by the formula (1), or the oxazolidine compound and a ketimine compound synthesized from a ketone or an aldehyde represented by the formula (2) and a polyamine.

Fourth aspect: a moisture-curable epoxy resin composition comprising a polyepoxy compound, an oxazolidine compound and/or a ketimine compound, and a silyl phosphate ester and/or an acidic phosphoric acid.

Fifth aspect: a moisture-curable epoxy resin composition comprising a polyepoxy compound and an oxazolidine compound represented by the formula (16).

The resin composition according to the second, fourth, and fifth aspects of the present invention is hereinafter referred to as the composition of the present invention.

[1] Major Components Included in the Compositions of the Present Invention

<Polyepoxy Compound>

Exemplary polyepoxy compounds which may be used in the present invention include polyepoxy compounds having polyether structure and containing two or more epoxy groups in one molecule such as glycidyl ether epoxy resins of bisphenol A and derivatives thereof, glycidyl ether epoxy resins of glycerin, glycidyl ether epoxy resins of polyalkylene oxide, glycidyl ether epoxy resins of phenol novolac, glycidyl ether epoxy resins of dimeric acid, and glycidyl ether epoxy resins of bisphenol F; polyepoxy compounds having polyester structure such as glycidyl ester epoxy compound of urethane-modified epoxy compound; and polyepoxy compounds having polysulfide structure wherein the main chain contains —(R—$S_x$)— as the recurring unit and epoxy group is present at the terminal of the molecule, wherein R is an alkylene group containing 2 to 8 carbon atoms optionally containing oxygen atom in its main chain and x is 1 to 3. If necessary, such polyepoxy compound may be used in combination with a monofunctional epoxy compound such as phenylglycidylether.

Among these, use of a glycidyl ether epoxy resin of bisphenol A as a universal epoxy resin is preferable.

<Curing Accelerator>

The composition of the present invention may optionally contain a curing accelerator, and use of a phosphite ester for the curing accelerator is effective since incorporation of a phosphite ester does not result in adverse effects such as viscosity increase during the storage of the present composition.

Exemplary phosphite esters which may be used as a curing accelerator include triphenyl phosphite, tris(nonylphenyl) phosphite, triethyl phosphite, tributyl phosphite, tris(2-ethylhexyl) phosphite, tridecyl phosphite, tris (tridecyl) phosphite, diphenylmono(2-ethylhexyl) phosphite, diphenylmonodecyl phosphite, diphenyl-mono (tridecyl) phosphite, tetraphenyldipropylene glycol diphosphite, tetraphenyltetra(tridecyl)pentaerythritol tetraphosphite, trilauryl trithiophosphite, bis(tridecyl) pentaerythritol diphosphite, bis(nonyl-phenyl) pentaerythritol diphosphite, tristearyl phosphite, distearyl pentaerythritol diphosphite, tris(2,4-di-t-butylphenyl) phosphite, hydrogenated bisphenol A pentaerythritol phosphite polymer and other triesters. Other exemplary phosphite esters are di- or monoesters produced by partially hydrolyzing the triesters as described above. Among these, use of tetraphenyl-tetra(tridecyl)pentaerythritol tetraphosphite, bis(tridecyl)pentaerythritol diphosphite, bis (nonyl-phenyl)pentaerythritol diphosphite, distearyl pentaerythritol diphosphite, hydrogenated bisphenol A pentaerythritol phosphite polymer, and the like is preferable in view of their high capability in accelerating the curing.

When a triester is used among the phosphite esters as described above, the triester is incorporated at an amount of at least 0.005% by mole, and preferably 0.005% by mole to 1.0% by mole in relation to the epoxy group in the polyepoxy compound. When the triester is used at amount within such range, sufficient action as an accelerator is realized without detracting from the storage stability of the composition.

The composition of the present invention may also contain an accelerator other than the phosphite ester.

<Silane Coupling Agent>

The composition of the present invention may optionally contain a silane coupling agent. Inclusion of the silane coupling agent enables production of the resin composition exhibiting good balance between the storage stability and the curing speed as well as improved adhesion to wet surface.

The silane coupling agent used is not limited to any particular type, and any conventional silane coupling agent may be employed. Exemplary silane coupling agents include chloropropyltrimethoxysilane, trimethoxyvinylsilane, vinyltriethoxysilane, vinyltris(2-methoxyethoxy)silane, r-methacryloxypropyltrimethoxysilane, and 3-glicydoxypropyltrimethoxysilane. Among these, use of trimethoxyvinylsilane and 3-glicydoxypropyltrimethoxysilane is preferred since use of such silane coupling agents is favorable in view of their excellent ability in improving the adhesion to wet surface and their general versatility.

The silane coupling agent is incorporated preferably at an amount of 0.1 part by weight to 20 parts by weight, and more preferably, at an amount of 0.5 part by weight to 10 parts by weight per 100 parts by weight of the polyepoxy compound. When the silane coupling agent is used at an amount in such range, the resulting composition will exhibit improved adhesion to wet surface, and more illustratively, high shear stress at break as well as percentage of matrix failure of almost 100%.

<Calcium Carbonate>

The composition of the present invention may optionally contain calcium carbonate at an amount that does not detract from the objects of the present invention. In particular, addition of a surface-treated calcium carbonate is beneficial for enabling viscosity adjustment and realizing good initial thixotropy and storage stability.

Exemplary such calcium carbonate products include conventional known surface-treated calcium carbonate products such as calcium carbonate surface treated with a fatty acid, a resinous acid, a fatty acid ester or a urethane compound synthesized from a polyisocyanate compound and a hydroxy compound. Typical calcium carbonate products surface treated with a fatty acid include Calfine 200 (manufactured by Maruo Calcium K. K.) and White-in 305 (heavy calcium carbonate, manufactured by Shiraishi Calcium). A typical calcium carbonate product surface treated with a fatty acid ester include Sealet 200 (manufactured by Maruo Calcium).

The calcium carbonate is preferably used at an amount of 30 to 200 parts by weight, and more preferably at an amount of 50 to 150 parts by weight per 100 parts by weight of polyepoxy compound. When the calcium carbonate is used at an amount in such range, an adequate initial thixotropy and sufficient workability are likely to be realized with no excessive increase in viscosity.

<Other Additives>

The composition of the present invention may contain additives other than the compounds as described above at an amount that does not detract from the object of the present invention for example, a filler, a plasticizer, a thixotropic agent, a pigment, a dye, an antiaging agent, an antioxidant, an antistat, a flame retardant, a tackifier, a dispersant, and a solvent.

The fillers which may be used in the present invention include organic and inorganic fillers of any configuration. Exemplary fillers include fumed silica, calcined silica, precipitated silica, pulverized silica, fused silica; diatomaceous earth; iron oxide, zinc oxide, titanium oxide, barium oxide, magnesium oxide; calcium carbonate, magnesium carbonate, zinc carbonate; talc clay, kaolin clay, calcined clay; carbon black; and any of the foregoing treated with a fatty acid, resinous acid, or fatty acid ester.

The plasticizers which may be used in the present invention include dioctyl phthalate (DOP), dibutyl phthalate (DBP), dioctyl adipate, isodecyl succinate, diethylene glycol dibenzoate, pentaerythritol ester; butyl oleate, methylacetyl ricinoleate; tricresyl phosphate; trioctyl phosphate; adipic propylene glycol polyester, and adipic butyleneglycolpolyester. Such plasticizer may be used alone or in combination of two or more.

The thixotropic agents which may be used in the present invention include Aerosil (manufactured by Japan Aerosil K. K.) and Disparon (manufactured by Kusumoto Kasei K. K.); and the antistatic agents which may be used in the present invention include quaternary ammonium salt, and a hydrophilic compound such as polyglycol and an ethylene oxide derivative.

The pigments which may be used in the present invention include both inorganic and organic pigments. Exemplary inorganic pigments include titanium dioxide, zinc oxide, ultramarine, red oxide, lithopone, lead, cadmium, iron, cobalt, aluminum, hydrochloride, sulfate, and the like.

The organic pigments which may be used in the present invention include azo pigment, copper phthalocyanine pigment, and the like.

The antiaging agents which may be used in the present invention include hindered phenol compounds.

The antioxidants which may be used in the present invention include butylhydroxytoluene (BHT), butylhydroxyanisole (BHA), and the like.

The flame retardants which may be used in the present invention include chloroalkylphosphates, dimethyl methylphosphonate, bromine and phosphor compounds, ammonium polyphosphate, neopentylbromide-polyether, brominated polyether, and the like.

The tackifiers which may be used in the present invention include terpene resin, phenol resin, terpene-phenol resin, rosin resin, xylene resin, and the like.

[2] The Compositions of the Present Invention

<1>First Aspect of the Present Invention

The oxazolidine compound according to the first aspect of the present invention is a compound represented by the formula (1):

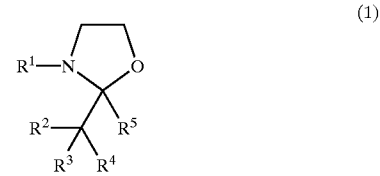

wherein $R^1$ is methyl group or ethyl group;

$R^2$ is an alkyl group containing 1 to 6 carbon atoms;

$R^3$ is methyl group or ethyl group;

$R^4$ is hydrogen atom, methyl group, or ethyl group;

and

R[5] is hydrogen atom or a hydrocarbon group containing 1 to 6 carbon atoms;

with the proviso that R[2], R[3] and R[4] may together represent an alicyclic ring or an aromatic ring; and that R[3] and R[5] may together represent an alicyclic ring or an aromatic ring.

The oxazolidine compound according to the first aspect of the present invention has a bulky substituent around the nitrogen atom in the heterocyclic ring, and the nitrogen in the heterocyclic ring is protected through steric hindrance by the substituent, and consequently, basicity of the compound is markedly reduced. Therefore, the moisture-curable resin composition produced by using the oxazolidine compound according to the first aspect of the present invention for the latent curing agent enjoys an excellent storage stability.

The moisture-curable resin composition produced by using the oxazolidine compound according to the first aspect of the present invention for the latent curing agent also exhibits a long "tack free time", and a prolonged time is thereby allowed for the water required in the hydrolysis of the oxazolidine compound to impregnation into the coated composition. Therefore, the composition exhibits markedly improved depth curability, and thickness of the film to be cured can be readily increased.

Therefore, the oxazolidine compound according to the first aspect of the present invention is quite suitable for use as a latent curing agent in a moisture-curable resin composition such as one-part epoxy resin composition.

The oxazolidine compound according to the first aspect of the present invention is a composition represented by the formula (1) as described above.

Typical examples of the alkyl group containing 1 to 6 carbon atoms represented by the R[2] are methyl group, ethyl group, propyl group, butyl group, pentyl group, and hexyl group.

Of the hydrogen atom and the hydrocarbon group containing 1 to 6 carbon atoms which may be represented by the R[5], examples of the hydrocarbon group containing 1 to 6 carbon atoms include alkyl groups containing 1 to 6 carbon atoms, such as methyl group, ethyl group, propyl group, isopropyl group, butyl group, isobutyl group, s-butyl group, t-butyl group, pentyl group, isopentyl group, neopentyl group, t-pentyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, and 1-ethyl-2-methylpropyl group, and alkylene group corresponding to each of the above-listed alkyl groups. Among these, alkyl groups containing 1 to 6 carbon atoms are preferable as the hydrocarbon group containing 1 to 6 carbon atoms.

The oxazolidine compound according to the first aspect of the present invention is preferably a compound wherein said R[1] is methyl group in view of further improving the curing speed of the curable resin composition containing the oxazolidine compound as its latent curing agent, and preferably a compound wherein said R[2], R[3] and R[5] are respectively methyl group, and said R[4] is hydrogen atom in view of accelerating hydrolysis of the oxazolidine compound.

The oxazolidine compound according to the first aspect of the present invention can be obtained through synthesis by reacting a ketone represented by the following formula (3) and an aminoalcohol represented by the following formula (4):

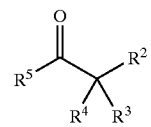

(3)

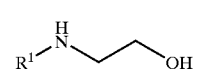

(4)

wherein R[1] to R[5] are as defined above for the formula (1).

The synthesis can be accomplished, for example, by reacting the ketone and the aminoalcohol through heating under reflux in the absence of the solvent or in the presence of benzene, toluene, xylene or other solvent, and azeotropically removing the separated water.

The oxazolidine compound according to the first aspect of the present invention enables production of a curable resin composition exhibiting satisfactory storage stability simultaneously with excellent depth curability when the oxazolidine compound is used as a latent curing agent of the composition.

<2>Second Aspect of the Present Invention

Next, the moisture-curable epoxy resin composition according to the second aspect of the present invention (which may be hereinafter referred to as the composition according to the second aspect of the present invention) is described.

The composition according to the second aspect of the present invention is a composition which comprises a polyepoxy compound having two or more epoxy groups on average in one molecule and an oxazolidine compound which is sterically hindered to a considerable degree. This composition enjoys both satisfactory storage stability and excellent depth curability.

The polyepoxy compound which may be used in the second aspect of the present invention are the same as those referred in the section of "[1]<Polyepoxy compound>", above. Among such polyepoxy compounds, the preferred is glycidyl ether epoxy resin of bisphenol A as a universal epoxy resin.

In view of further improving the storage stability of the composition according to the second aspect of the present invention, the amount of hydroxyl group in the skeleton of the polyepoxy compound used in the second aspect of the present invention is preferably up to 10% by mole, and more preferably from 0% by mole to 8% by mole. When the hydroxyl content in the skeleton is within such range, the storage stability of the moisture-curable epoxy resin composition is further improved. It should be noted that the hydroxyl group in the skeleton of the polyepoxy compound designates both the hydroxyl group generated by ring opening of the epoxy ring in the synthesis of the polyepoxy compound, and the hydroxyl group present as left unreacted from the polyol which was used as a starting material. It should be also noted that the language "the amount of hydroxyl group in the skeleton of the polyepoxy compound is up to 10% by mole" include the case wherein hydroxyl group is utterly absent in the skeleton of the polyepoxy compound.

The composition according to the second aspect of the present invention also contains an oxazolidine compound according to the first aspect of the present invention represented by the formula (1) as its latent curing agent.

The oxazolidine compound used in this invention for the latent curing agent has a bulky substituent around the nitrogen atom in the heterocyclic ring as described in the section of "<1>First aspect of the present invention", and therefore, the composition according to the second aspect of the present invention enjoys satisfactory storage stability as well as excellent depth curability.

The oxazolidine compound used in the second aspect of the present invention is a compound represented by formula (1) and the definition of the $R^1$ to $R^5$, the details of the preferred embodiments, and the production process of the composition represented by the formula (1) described in "<1>first aspect of the present invention" also applies to the oxazolidine compound used in the second aspect of the present invention.

In the composition according to the second aspect of the present invention, the oxazolidine compound is preferably used at an amount such that the molar ratio of the epoxy group/the oxazolidine ring is in the range of 0.5 to 10, and more preferably, 1 to 6, since the composition exhibits sufficient storage stability and satisfactory depth curability when the molar ratio is within such range.

The composition according to the second aspect of the present invention may further comprise a ketimine compound synthesized from a ketone or an aldehyde represented by formula (2):

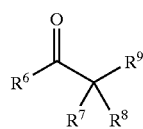

(2)

wherein
$R^6$ is hydrogen atom or methyl group;
$R^7$ is an alkyl group containing 1 to 6 carbon atoms;
$R^8$ is methyl group or ethyl group; and
$R^9$ is hydrogen atom, methyl group, or ethyl group;
with the proviso that $R^7$, $R^8$ and $R^9$ may together represent an alicyclic ring or an aromatic ring; and that $R^6$ and $R^7$ may together represent an alicyclic ring or an aromatic ring; and a polyamine.

The ketone or the aldehyde used in the synthesis of the ketimine compound is a ketone or an aldehyde which has a substituent at its α position and which is sterically hindered to a considerable degree. The ketone or the aldehyde which has a substituent at its α position is a ketone or an aldehyde which has a substituent at α position from the carbonyl group, and the ketimine compound synthesized by using such ketone or aldehyde has a bulky substituent near the double bond of the ketimine group and the contradictory properties of the curing speed and the storage stability are thereby satisfied. More specifically, in the case of a ketimine group-containing compound which has been produced by using methyl isopropyl ketone, methyl t-butylketone, or the like which has a substituent at α position of the carbonyl carbon of the ketone or the aldehyde for the starting material, basicity of the compound is by far weakened through protection of the ketimine nitrogen by the substituent, namely, by the steric hindrance. Therefore, a composition prepared by using such ketimine compound with the epoxy resin is stable since the composition is not affected by the ketimine group-containing compound.

On the other hand, when the epoxy resin composition containing the ketimine group-containing compound which has been produced by using a ketone or an aldehyde which has a substituent at α position of the carbonyl carbon is brought into air, the ketimine nitrogen is easily attacked by the small-sized water molecule of the moisture since such small-sized molecule is not sterically hindered by the substituent. As a consequence, the composition rapidly undergoes hydrolysis, and the curing speed of the epoxy resin composition is quite fast.

Accordingly, the composition according to the second aspect of the present invention which also includes the ketimine compound synthesized by using such ketone or aldehyde as its latent curing agent exhibits highly improved curing speed with the storage stability and depth curability retained at sufficient level.

The ketone or the aldehyde used for the synthesis of the ketimine compound may be a compound represented by the formula (2) wherein the alkyl group containing 1 to 6 carbon atoms represented by the $R^7$ may be methyl group, ethyl group, propyl group, butyl group, pentyl group, hexyl group, or the like. Typical examples of such ketone are methyl isopropyl ketone and methyl t-butyl ketone.

The polyamine used for the synthesis of the ketimine compound as described above is not limited to any particular type, and use of an aliphatic polyamine is preferable in view of the high curing speed.

Exemplary polyamines include 2,5-dimethyl-2,5-hexamethylenediamine, menthene diamine, 1,4-bis(2-amino-2-methylpropyl)piperadine, polypropylene glycol (PPG) wherein propylene branched carbons at opposite ends of the molecule has amino group bonded thereto (Jeffamine D230 and Jeffamine D400 manufactured by Sun Technochemical), ethylenediamine, propylenediamine, butylenediamine, diethylenetriamine, triethylenetetramine, tetraethylenepentamine, pentaethylenehexamine, hexamethylenediamine, trimethylhexamethylenediamine, N-aminoethylpiperadine, 1,2-diaminopropane, iminobispropylamine, methyliminobispropylamine, diamine having polyether skeleton wherein amine nitrogen has methylene group boded thereto, for example, $H_2N(CH_2CH_2O)_2(CH_2)_2NH_2$ (trade name, Jeffamine EDR148, manufactured by Sun Technochemical), 1,5-diamino-2-methylpentane (trade name, MPMD, manufactured by DuPont Japan), metaxylylene diamine (MXDA), polyamide amine having amino group at the terminal of the polyamide molecule (X2000, manufactured by Sanwa Chemical), isophorone diamine,
1,3-bisaminomethylcyclohexane (1,3BAC, manufactured by Mitsubishi Gas Chemical), 1-cyclohexylamino-3-aminopropane, 3-aminomethyl-3,3,5-trimethyl-cyclohexylamine, a dimethyleneamine having norbornane skeleton (NBDA, manufactured by Mitsui Chemical). Among these, use of 3-bisaminomethylcyclohexane (1,3BAC), a dimethyleneamine having norbornane skeleton (NBDA), metaxylylene diamine (MXDA), Jeffamine EDR148 (trade name), and polyamide amine is preferable.

In view of improving the storage stability and the curability of the composition according to the second aspect of the present invention by incorporating the ketimine compound, examples of the preferable ketimine compound are:
ketimines produced from methyl isopropyl ketone (MIPK) or methyl t-butyl ketone (MTBK) and Jeffamine EDR148 (trade name, a dimethyleneamine having polyether skeleton);
ketimines produced from methyl isopropyl ketone (MIPK) or methyl t-butyl ketone (MTBK) and 1,3-bisaminomethylcyclohexane (1,3BAC);

ketimines produced from methyl isopropyl ketone (MIPK) or methyl t-butyl ketone (MTBK) and a dimethyleneamine having norbornane skeleton (tradename, NBDA);

ketimines produced from methyl isopropyl ketone (MIPK) or methyl t-butyl ketone (MTBK) and metaxylylenediamine (MXDA); and ketimines produced from methyl isopropyl ketone (MIPK) or methyl t-butyl ketone (MTBK) and polyamide amine (X2000).

Among these, use of the ketimine produced from MIPK or MTBK and NBDA, and the ketimine produced from MIPK and 1,3BAC results in the improved curability of the resulting composition.

Use of the ketimine produced from MIPK or MTBK and X2000 results in the improved adhesion to wet surface of the resulting composition.

The ketimine compound as described above may be produced by reacting the ketone or the aldehyde and the polyamine through heating under reflux in the absence of the solvent or in the presence of benzene, toluene, xylene or other solvent, and azeotropically removing the separated water.

In the composition according to the second aspect of the present invention, the ketimine compound is preferably used at an amount such that the molar ratio of the epoxy group/imino group in the ketimine compound is in the range of 0.5 to 5, and more preferably, 1 to 3. When the ketimine compound is used at such an amount, the storage stability and the curability of the composition of the present invention can be improved with the depth curability retained at an acceptable level.

In addition to the polyepoxy compound, the oxazolidine compound represented by the formula (1), and the ketimine compound, the composition according to the second aspect of the present invention may also contain a curing accelerator, a silane coupling agent, calcium carbonate (including surface-treated calcium carbonate), and other additives such as a filler, a plasticizer, a thixotropic agent, a pigment, a dye, an antiaging agent, an antioxidant, an antistat, a flame retardant, a tackifier, a dispersant, and a solvent at an amount which does not detract from the objects of the present invention.

The curing accelerator, silane coupling agent, calcium carbonate, and other additives used may be the same as those described in the sections of "[1]<Curing accelerator >, <Silane coupling agent>, <Calcium carbonate>, and <Other additives>" at the amount described therein.

The method for producing the composition according to the second aspect of the present invention is not particularly limited. The composition, however, is preferably produced by thoroughly kneading and uniformly dispersing the components as described above in a mixer or other agitating means under reduced pressure or in an inert atmosphere such as nitrogen.

The moisture-curable epoxy resin composition according to the second aspect of the present invention contains an oxazolidine compound for the latent curing agent, and consequently, it exhibits excellent storage stability as well as excellent depth curability and it can be formed into a cured film of any desired thickness. This composition is quite suitable for use as an adhesive, a sealant, a coating composition, and the like.

Although the composition according to the second aspect of the present invention has been described as a one-part epoxy resin composition, it should be understood that, in the use of the composition, the composition according to the second aspect of the present invention can also be used as a two-part epoxy resin composition.

<3>Third Aspect of the Present Invention

Next, the latent curing agent according to the third aspect of the present invention (which may be hereinafter referred to as the latent curing agent of the present invention) is described.

The latent curing agent of the present invention contains the oxazolidine compound represented by the formula (1) according to the first aspect of the present invention. The latent curing agent of the present invention is quite useful as a latent curing agent which can realize satisfactory storage stability and depth curability of the resulting composition since the latent curing agent of the present invention contains the oxazolidine compound having a bulky substituent around the nitrogen in the heterocyclic ring as described above.

The description for the oxazolidine compound according to the first aspect of the present invention also applies to the oxazolidine compound used in the latent curing agent of the present invention.

The latent curing agent of the present invention may further contain a ketimine compound which is the one optionally employed in the composition according to the second aspect of the present invention. Since such highly sterically hindered ketimine compound as described above is incorporated, the latent curing agent of the present invention can be adequately used in the curable composition and realize sufficient storage stability and good depth curability of the composition as well as improved curing speed of the composition.

The description for the ketimine compound according to the second aspect of the present invention also applies to the ketimine compound used in the latent curing agent of this invention.

In view of improving the curing speed of the composition including the latent curing agent of the present invention while retaining the good storage stability and depth curability of the composition, the content of the ketimine compound in the latent curing agent of the present invention is preferably 5 parts by weight to 90 parts by weight per 100 parts by weight of the latent curing agent.

The latent curing agent of the present invention can be used in combination with other known latent curing agent.

The latent curing agent according to the third aspect of the present invention contains the oxazolidine compound of the first aspect of the present invention, and therefore, the composition is imparted with good storage stability and sufficient depth curability. Furthermore, when the latent curing agent according to the third aspect of the present invention contains the ketimine compound, the composition is imparted not only with the good storage stability and sufficient depth curability but also with improved curing speed.

<4>Fourth Aspect of the Present Invention

Next, the moisture-curable epoxy resin composition according to the fourth aspect of the present invention (hereinafter referred to as the composition according to the fourth aspect of the present invention) is described. The composition according to the fourth aspect of the present invention is an epoxy resin composition comprising a polyepoxy compound; an oxazolidine compound and/or ketimine compound; and a silyl phosphate ester and/or acidic phosphoric acid.

The polyepoxy compound used in the fourth aspect of the present invention may be the same as those described in the section of "[1]<Polyepoxy compound>". Among such polyepoxy compounds, the preferred is glycidyl ether epoxy resin of bisphenol A.

The oxazolidine compound used in the fourth aspect of the present invention is a compound having a saturated five-membered heterocyclic ring containing oxygen and nitrogen which undergoes ring opening in the presence of moisture (water) to react with epoxy group for curing. Exemplary oxazolidine compounds include oxazolidine compounds such as N-hydroxyalkyloxazolidine as well as oxazolidine derivatives such as oxazolidine silylether, carbonate oxazolidine, ester oxazolidine, and the like. Among these, the oxazolidine compound produced from a ketone represented by formula (10) is preferable in view of simultaneously realizing the curability and the storage stability.

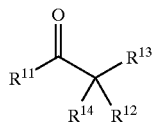
(10)

In formula (10), $R^{11}$ is hydrogen atom or an alkyl group containing 1 to 6 carbon atoms;

$R^{12}$ is methyl group or ethyl group;

$R^{13}$ is an alkyl group containing 1 to 6 carbon atoms; and $R^{14}$ is hydrogen atom or an alkyl group containing 1 to 6 carbon atoms and is preferably hydrogen atom, methyl group or ethyl group;

with the proviso that $R^{12}$, $R^{13}$, and $R^{14}$ may together represent an alicyclic ring or an aromatic ring; and that $R^{11}$ and $R^{12}$ may together represent an alicyclic ring or an aromatic ring.

The oxazolidine compound obtained from the ketone represented by formula (10) is represented by formula (11):

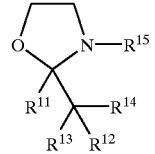
(11)

wherein $R^{11}$ is hydrogen atom or an alkyl group containing 1 to 6 carbon atoms;

$R^{12}$ is methyl group or ethyl group;

$R^{13}$ is an alkyl group containing 1 to 6 carbon atoms;

$R^{14}$ is hydrogen atom or an alkyl group containing 1 to 6 carbon atoms and is preferably hydrogen atom, methyl group or ethyl group; and $R^{15}$ is hydrogen atom, an alkyl group or a hydroxyalkyl group containing 1 to 6 carbon atoms, or a hydrocarbon group containing silylether, carbonate or ester group and is preferably methyl group or ethyl group;

with the proviso that $R^{12}$, $R^{13}$, and $R^{14}$ may together represent an alicyclic ring or an aromatic ring, and that $R^{11}$ and $R^{12}$ may together represent an alicyclic ring or an aromatic ring.

Such oxazolidine compound is synthesized through reaction between an aminoalcohol and a ketone by a known process.

Exemplary preferable aminoalcohols which may used include N-methylethanolamine, N-ethylethanolamine, and N-methylisopropanolamine, and use of N-methylethanolamine is particularly preferable in view of high curing speed.

Exemplary ketones represented by formula (10) include methyl ethyl ketone, methyl isobutyl ketone, methyl isopropyl ketone, methyl t-butyl ketone, diisopropyl ketone, methyl cyclohexyl ketone, and methylcyclohexanone, and among these, methyl isopropyl ketone and methyl t-butyl ketone, and in particular, methyl isopropyl ketone is preferable in view of good balance between the curing speed and the storage stability.

The oxazolidine compound is preferably used in the composition according to the fourth aspect of the present invention at an amount such that the molar ratio of [epoxy group/nitrogen atom in the oxazolidine compound] is in the range of 0.1 to 20, and more preferably, 0.5 to 5. When the molar ratio is less than 0.1, unreacted oxazolidine compound will remain in the system and adversely affect the physical properties of the resulting composition. When the molar ratio is in excess of 20, the resulting composition will suffer from insufficient curing due to insufficiency of the curing agent.

The ketimine compound used in the composition according to the fourth aspect of the present invention may be any known ketimine compound, and the ketimine compound acts as a curing agent for the epoxy resin. Among the ketimine compounds which may be used, use of the ketimine obtained by reacting a ketone represented by formula (10) with a polyamine represented by formula (12) having at least two amino groups having methylene at its a position in the molecule is preferable in view of the good balance between the storage stability and the curability when used in a one-part composition. The ketone represented by formula (10) wherein $R^{11}$ is preferably hydrogen atom or methyl group and $R^{14}$ is preferably hydrogen atom, methyl group or ethyl group is used in the synthesis of the ketimine compound.

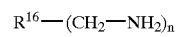
(12)

In formula (12), $R^{16}$ is an organic group which may contain a hetero group; and n is an integer of two or more.

The ketimine group obtained from the ketone represented by formula (10) and the polyamine represented by formula (12) has a bulky substituent near the double bond of the ketimine group as in the case of the ketimine compound employed in the second aspect of the present invention, and the contradictory properties of the curing speed and the storage stability required for a latent curing agent are thereby satisfied by the same mechanism as the ketimine compound used in the second aspect of the present invention.

Exemplary ketones represented by formula (10) include methyl ethyl ketone, methyl isobutyl ketone, methyl isopropyl ketone, methyl t-butyl ketone, diisopropyl ketone, methyl cyclohexyl ketone, and methylcyclohexanone, and among these, the preferred are methyl isopropyl ketone and methyl t-butyl ketone, and in particular, methyl isopropyl ketone in view of the good balance between the curing speed and the storage stability.

Exemplary polyamines represented by the formula (12) which have at least two amino groups having methylene at α position include aliphatic polyamines such as ethylenediamine, propylenediamine, butylenediamine, diethylenetriamine, triethylenetetramine, tetraethylenepentamine, pentaethylenehexamine, hexamethylenediamine, trimethylhexamethylenediamine, 1,2-diaminopropane, iminobispropylamine, methyliminobispropylamine, diamine having polyether skeleton as exemplified by Jeffamine EDR148 manufactured by Sun Technochemical, and MPMD manufactured by DuPont Japan; alicyclic amines such as isophorone diamine, 1,3-bisaminomethylcyclohexane, 1-cyclohexylamino-3-aminopropane, and 3-aminomethyl-3,3,5-trimethyl-cyclohexylamine, a diamine having norbornane skeleton as exemplified by NBDA manufactured by Mitsui Chemical; metaxylylene diamine, and a polyamide amine having amino group at the terminal of the polyamide molecule. Among these, use of 1,3-bisaminomethylcyclohexane (1,3BAC), norbornane diamine (NBDA), metaxylylene diamine (MXDA), Jeffamine EDR148 (trade name), and polyamide amine is preferable.

The ketimine compound used in the fourth aspect of the present invention can be synthesized by the method which is the same as the one used for synthesizing the ketimine compound used in the composition according to the second aspect of the present invention.

In the fourth aspect of the present invention, the ketimine compound is used at an amount such that the molar ratio of [epoxy group/imino group in the ketimine compound] is in the range of 0.2 to 20, preferably 0.5 to 10, and more preferably 1.0 to 5.

In the fourth aspect of the present invention, the oxazolidine compound and the ketimine compound may be used either alone or in combination. When the oxazolidine compound and the ketimine compound are used in combination, the amount of the oxazolidine compound and the ketimine compound used in relation to the epoxy resin may be adequately adjusted, and for example, when emphasis is laid on the storage stability, content of the oxazolidine compound is set at a higher value, and when emphasis is laid on fast curing property at some sacrifice of the storage stability, the content of the ketimine compound is set at a higher value. For example, as will be apparent from the comparison between Example 1 and Example 3, below, a resin composition containing 20 parts by weight of the oxazolidine compound and 20 parts by weight of the ketimine compound per 100 parts by weight of epoxy resin was inferior in storage stability but faster in curing by 1 day compared to the resin composition containing 40 parts by weight of the oxazolidine compound in relation to 100 parts by weight of epoxy resin.

The silyl phosphate ester used in the fourth aspect of the present invention is a composition represented by formula (8) which may be either a monomer or a polymer and which may be a low molecular weight compound or a high molecular weight compound.

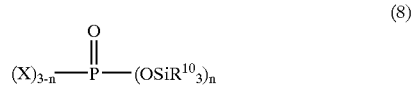

(8)

In formula (8), R is an alkyl group containing 1 to 6 carbon atoms; X is an organic group which may contain a hetero atom such as methyl group, ethyl group, octyl group or other alkyl group; methoxy group, ethoxy group, buthoxy group, hexaoxy group, 2-ethylhexaoxy group, octadecyloxy group ($CH_3(CH_2)_{17}O$—) or other alkoxy group; a trimethyl-silyloxy group, or the like which may contain S; and n is an integer of from 1 to 3. When n is two or more, $R^{10}$ may respectively represent either the same or different substituents. When 3-n is two or more, X may respectively represent either the same or different substituents.

The silyl phosphate ester used in the fourth aspect of the present invention is most preferably the silyl phosphate ester wherein $R^{10}$ is methyl group in the formula (8) in view of ease of silylation and hydrolysis of the phosphate compound.

The silyl phosphate ester represented by formula (8) can be produced, for example, by reacting the corresponding phosphate with a trialkylchlorosilane or an alkylsilazane.

The silyl phosphate ester represented by formula (8) in the composition according to the fourth aspect of the present invention is hydrolyzed by the moisture in the air to produce phosphoric acid, and the phosphoric acid promotes ring opening of the oxazolidine compound which is the latent curing agent of the epoxy resin. The curing of the epoxy resin is thereby accelerated. As a consequence, curing speed of the composition according to the fourth aspect of the present invention can be adjusted by increasing or decreasing the content of the silyl phosphate ester in the composition.

As will be apparent, for example, from the comparison between Example 2-1 and Comparative Example 2-1, below, curing time can be shortened without detracting from the storage stability when 1 part by weight of trimethyl silyl ester of dioctyl phosphate which is a silyl phosphate is incorporated per 100 parts by weight of epoxy resin.

The acidic phosphoric acid used in the fourth aspect of the present invention is a compound having a chemical structure represented by formula (9) which may be a monomer or oligomer.

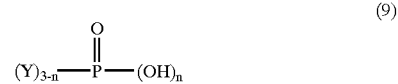

(9)

In the formula, Y is an organic group which may contain a hetero atom such as methyl group, ethyl group, octyl group or other alkyl group; methoxy group, ethoxy group, buthoxy group, hexaoxy group, 2-ethylhexaoxy group, or octadecyloxy group ($CH_3(CH_2)_{17}O$—) or other alkoxy group; a trimethyl-silyloxy group, or the like which may contain S; Y may be OH, and n is an integer of from 1 to 3.

The acidic phosphoric acid represented by formula (9) in the composition according to the fourth aspect of the present invention promotes ring opening of the oxazolidine compound which is the latent curing agent of the epoxy resin as in the case of the silyl phosphate ester as described above. The curing, and in particular, curing of the surface portion of the epoxy resin is thereby accelerated. The curability of the composition according to the fourth aspect of the present invention can be adjusted by increasing or decreasing the content of the acidic phosphoric acid in the composition.

As will be apparent, for example, from the comparison between Example 2—2 and Comparative Example 2-1, below, curing time can be shortened without detracting from the storage stability when 1 part by weight of dioctylphosphate which is an acidic phosphoric acid is incorporated per 100 parts by weight of epoxy resin. As will be apparent, for example, from the comparison between Example 2-1 and Example 2—2, it is to be noted that a dioctylphosphate which is not blocked by silyl group can shorten the curing time to a higher extent compared to the dioctylphosphate which is blocked with silyl group when they are incorporated at a same equivalent in relation to the epoxy resin.

The silyl phosphate ester or the acidic phosphoric acid is preferably used at a content in the range of 0.01 to 20 parts by weight, more preferably 0.05 to 10 parts by weight, and still more preferably 0.1 to 5 parts by weight per 100 parts by weight of the epoxy resin. When the content is less than 0.01 part by weight, the curing speed will not be sufficiently improved. When the content is in excess of 20 parts by weight, the cured product will suffer from insufficient physical properties and the one-part composition will suffer from insufficient storage stability.

Presence of the silyl phosphate ester or the acidic phosphoric acid promotes ring opening of the oxazolidine compound which is the latent curing agent, and in turn, curing of the epoxy resin, and in particular, curing of the surface portion of the composition.

In the fourth aspect of the present invention, either one or both of the silyl phosphate ester and the acidic phosphoric acid may be used in the composition. When both are used, their content in relation to the epoxy resin may be adequately adjusted.

In addition to the polyepoxy compound, the oxazolidine compound and/or the ketimine compound, and the silyl phosphate ester and/or the acidic phosphoric acid, the composition according to the fourth aspect of the present invention may also contain other additives such as a curing accelerator, a silane coupling agent, calcium carbonate, a filler, a plasticizer, a thixotropic agent, a pigment, a dye, an antiaging agent, an antioxidant, an antistat, a flame retardant, a tackifier, a dispersant, and a solvent at an amount which does not detract from the objects of the present invention.

The curing accelerator, silane coupling agent, calcium carbonate, and other additives used may be the same as those described in the sections of "[1]<Curing accelerator>, <Silane coupling agent>, <Calcium carbonate>, and <Other additives>".

Production of the composition according to the fourth aspect of the present invention can be accomplished by adding the oxazolidine compound and/or the ketimine compound and the silyl phosphate ester and/or the acidic phosphoric acid to the polyepoxy compound with other optional additives and thoroughly kneading the mixture.

The resulting composition according to the fourth aspect of the present invention has excellent storage stability as well as excellent curability, and in particular, excellent surface curability.

The composition according to the fourth aspect of the present invention can be suitably used in an adhesive, a sealant, a primer and the like.

Although the composition according to the fourth aspect of the present invention has been described as a one-part epoxy resin composition, it should be understood that the composition according to the fourth aspect of the present invention can also be used as a two-part epoxy resin composition.

<5>Fifth Aspect of the Present Invention

Next, the moisture-curable epoxy resin composition according to the fifth aspect of the present invention (hereinafter referred to as the composition according to the fifth aspect of the present invention) is described.

The composition according to the fifth aspect of the present invention is a curable resin composition comprising a polyepoxy compound having at least two epoxy groups in the molecule; and an oxazolidine compound represented by formula (16) as will be described later.

The polyepoxy compound used in the fifth aspect of the present invention may be the same as those described in the section of "[1]<Polyepoxy compound>". Among such polyepoxy compounds, the preferred is glycidyl ether epoxy resin of bisphenol A.

The oxazolidine compound used in the fifth aspect of the present invention is a compound represented by formula (16):

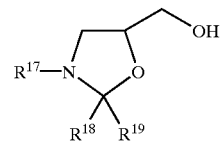

(16)

In formula (16), $R^{17}$ is a hydrocarbon group containing 1 to 6 carbon atoms, for example, an alkyl group containing 1 to 6 carbon atoms such as methyl group, ethyl group, propyl group, isopropyl group, butyl group, isobutyl group, s-butyl group, t-butyl group, pentyl group, isopentyl group, neopentyl group, t-pentyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, or 1-ethyl-2-methylpropyl group, or an alkenyl group corresponding to such alkyl group.

Among these, the oxazolidine compound is preferably the one wherein $R^{17}$ is methyl group or ethyl group in view of the particularly improved surface curability of the resulting composition according to the fifth aspect of the invention.

$R^{18}$ and $R^{19}$ are independently hydrogen atom or a hydrocarbon group containing 1 to 15 carbon atoms. Exemplary hydrocarbon group containing 1 to 15 carbon atoms include a straight-chain or branched alkyl group, an alkenyl group, an aryl group which may be substituted with one or two substituents, an arylalkyl group, and a cycloalkyl group which may be substituted with one or two substituents containing 1 to 15 carbon atoms. Examples include straight-chain alkyl groups such as methyl group, ethyl group, propyl group, butyl group, pentyl group, octyl group, dodecyl group, and lauryl group; branched alkyl groups such as isopropyl group, isobutyl group, s-butyl group, t-butyl group, isopentyl group, neopentyl group, t-pentyl group, 1-methylbutyl group, and 1-methylheptyl group; alkenyl groups such as vinyl group, allyl group, isopropenyl group, and 2-methylallyl group; aryl groups such as tolyl group (o-, m-, p-), dimethylphenyl group, and mesityl group; arylalkyl groups such as benzyl group, phenetyl group, and α-methylbenzyl group; cycloalkyl groups such as cyclopentyl group and cyclohexyl group.

Alternatively, $R^{18}$ and $R^{19}$ may together represent an alicyclic ring or an aromatic ring containing 4 to 10 carbon atoms. Exemplary such alicyclic rings containing 4 to 10 carbon atoms include cyclobutyl group, cyclopentyl group, cyclohexyl group, cycloheptyl group, and cyclooctyl group. Exemplary such aromatic rings containing 4 to 10 carbon atoms include phenyl group, benzyl group, tolyl group (o-, m-, p-), and xylyl group.

Among the functional groups as described above, $R^{18}$ is preferably a bulky substituent such as a branched hydrocarbon group or a hydrocarbon group containing an alicyclic or aromatic ring, for example isobutyl group or other branched alkyl group, an aryl group, an arylalkyl group, or a cycloalkyl group. The nitrogen atom in the heterocyclic ring (oxazolidine ring) will then be protected through steric hindrance by such substituent, and basicity of the nitrogen atom will be greatly reduced and the resulting composition according to the fifth aspect of the present invention will enjoy satisfactory storage stability.

Among the functional groups as described above, $R^{18}$ is most preferably a group whose first positioned carbon atom is a branched carbon or a ring member carbon in view of imparting a sufficient storage stability with the resulting composition according to the fifth aspect of the present invention. Examples of such $R^{18}$ whose first positioned carbon atom is a branched carbon include isopropyl group, s-butyl group, t-butyl group, t-pentyl group, 1-methylbutyl group, 1-methylheptyl group, and isopropenyl group. Examples of such $R^{18}$ whose first positioned carbon atom is a ring member carbon include aryl groups such as phenyl group, tolyl group (o-, m-, p-), dimethylphenyl group, and α-methylbenzyl group, and cycloalkyl groups such as cyclopentyl group, cyclohexyl group, and methylcyclohexyl group.

Among these, $R^{18}$ is most preferably isopropyl group, t-butyl group, or cyclohexyl group in view of their ease of availability and synthesis.

Among the oxazolidine compounds which may be used in the fifth aspect of the present invention, exemplary preferable oxazolidine compounds are those represented by formulae (17), (18), and (19):

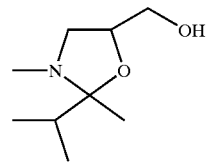

(17)

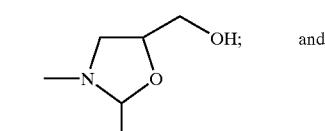

(18)

and

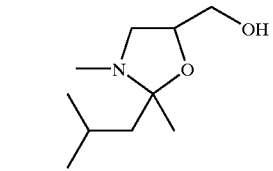

(19)

The oxazolidine compounds represented by the formula (16) may be used either alone or as a mixture of two or more types of such compounds.

The oxazolidine compound represented by the formula (16) undergoes ring opening in the presence of moisture (water) through hydrolysis to thereby react with the epoxy group and function as a latent curing agent for the polyepoxy compound. As a consequence, the composition according to the fifth aspect of the present invention containing the oxazolidine compound represented by the formula (16) enjoys an adequately prolonged tack free time to facilitate the water required in the hydrolysis of the oxazolidine compound to penetrate into the composition. It is believed that anionic polymerization is also induced by the tertiary amine generated after the surface curing although such anionic polymerization is yet to be confirmed. As a consequence, the composition according to the fifth aspect of the present invention exhibits excellent depth curability and thickness of the film to be cured can be readily increased. In addition, the oxazolidine compound represented by the formula (16) has a substituent which is preferably a bulky substituent whose first positioned carbon atom is a branched carbon or a ring member carbon around the nitrogen atom of the heterocyclic ring, and consequently, the composition according to the fifth aspect of the present invention containing such oxazolidine compound is quite excellent in storage stability.

In contrast to the epoxy resin composition containing a conventional oxazolidine compound which has been used for the latent curing agent, and which suffered from inferior surface curability and required several days for complete curing, the composition according to the fifth aspect of the present invention containing the oxazolidine compound of specific structure wherein fifth positioned ring member carbon in the heterocyclic ring is substituted with methylol group exhibits satisfactory surface curability since the oxazolidine compound represented by the formula (16) undergoes immediate hydrolysis.

The synthesis of the oxazolidine compound represented by the formula (16) to be incorporated in the composition according to the fifth aspect of the present invention can be accomplished by reacting the aminoalcohol represented by the following formula with the ketone or the aldehyde represented by the following formula through heating under reflux in the absence of the solvent or in the presence of benzene, toluene, xylene or other solvent, and azeotropically removing the separated water. In the following formulae, $R^{17}$, $R^{18}$ and $R^{19}$ are as defined above for the $R^{17}$, $R^{18}$ and $R^{19}$ of the formula (16).

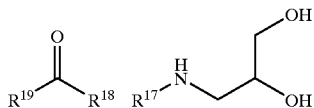

The oxazolidine compound is preferably used in the composition according to the fifth aspect of the present invention at an amount such that the molar ratio of [epoxy group/nitrogen atom in the oxazolidine compound] is in the range of 0.1 to 50, and more preferably, 0.5 to 10. When the molar ratio is within such range, the resulting composition according to the fifth aspect of the present invention will enjoy satisfactory surface curability and depth curability as well as sufficient storage stability.

The composition according to the fifth aspect of the present invention may further comprise a ketimine compound. When the ketimine compound is included, the composition according to the fifth aspect of the present invention exhibits improved surface curability and reduced surface curing time.

A ketimine compound is a compound produced by reacting a polyamine and a ketone, for example, by reacting a polyamine such as ethylenediamine, propylenediamine, butylenediamine, diethylenetriamine, triethylenetetramine, tetraethylenepentamine, or N-aminoethylpiperadine with a ketone such as methyl isobutyl ketone (MIBK), methyl ethyl ketone (MEK), methyl isopropyl ketone, methyl t-butyl ketone, methyl cyclohexyl ketone, methylcyclohexanone, propiophenone, or benzophenone.

The ketimine compound used in the fifth aspect of the present invention is preferably a compound wherein tertiary carbon or quaternary carbon is present at α position of the carbon atom and/or the nitrogen atom of ketimine bond (C═N). In other words, the ketimine compound used in the fifth aspect of the present invention is:

(1) a ketimine compound wherein tertiary or quaternary carbon is present at α position of the ketimine carbon, and tertiary carbon is present at α position of the ketimine nitrogen;

(2) a ketimine compound wherein tertiary or quaternary carbon is present at α position of the ketimine carbon, and secondary carbon is present at α position of the ketimine nitrogen; or (3) a ketimine compound wherein primary or secondary carbon is present at a position of the ketimine carbon, and tertiary carbon is present at α position of the ketimine nitrogen.

The ketimine compound having such structure has a bulky substituent near the ketimine bond, and basicity of the ketimine nitrogen is greatly reduced by the steric hindrance of such bulky substituent. Accordingly, the composition according to the fifth aspect of the present invention containing the ketimine compound of such structure is simultaneously excellent in surface curability and storage stability.

Among the preferable ketimine compounds as described above, the ketimine compounds described in (2) and (3) are particularly preferable in view of their ease of synthesis.

The ketimine compounds (1) may be synthesized by reacting a ketone having tertiary or quaternary carbon at α position of the ketone carbon with a polyamine having amino group having tertiary carbon at its α position.

The ketimine compounds (2) may be synthesized by reacting a ketone having tertiary or quaternary carbon at α position of the ketone carbon with a polyamine having amino group having secondary carbon at α position.

The ketimine compounds (3) may be synthesized by reacting a ketone having primary or secondary carbon at α position of the ketone carbon with a polyamine having amino group having tertiary carbon at α position.

The highly sterically hindered ketones which are preferable for use in synthesizing the preferable ketimine compound as described above include ketones having tertiary carbon at a position of the ketone carbon such as methyl isopropyl ketone, diisopropyl ketone, methyl cyclohexyl ketone, methylcyclohexanone, propiophenone, and benzophenone; and ketones having quaternary carbon at α position of the ketone carbon such as methyl t-butyl ketone.

Among these, the preferred are methyl isopropyl ketone (MIPK) and methyl t-butyl ketone (MTBK), and in particular, methyl isopropyl ketone in view of the good balance between the curing speed and the storage stability.

The polyamines having amino group wherein tertiary carbon is present at its α position which are preferable for use in synthesizing the preferable ketimine compound as described above include menthene diamine, metaphenylenediamine, diaminodiphenylmethane, diaminodiphenylsulfone, polypropylene glycol (PPG) wherein propylene branched carbons at opposite ends of the molecule has amino group bonded thereto (e.g. Jeffamine D230 and Jeffamine D400 manufactured by Sun Technochemical), Lamiron C-260, and Wandamin HM.

The ketones which may be used in synthesizing the preferable ketimine compound as described above in (3) include ketones having primary carbon at α position of the ketone carbon such as acetone, and ketones having secondary carbon at α position of the ketone carbon such as methyl ethyl ketone and methyl isobutyl ketone.

The polyamines having amino group having secondary carbon at its α position which may be used in synthesizing the preferable ketimine compound as described above in (2) include polyamines which has been described in the section of "<3>Third aspect of the present invention" as the polyamines having at least two amino groups having methylene at the α position in the molecule represented by formula (12).

Among the exemplary polyamines given, use of 1,3-bisaminomethylcyclohexane (1,3BAC), norbornane diamine (NBDA), metaxylylene diamine (MXDA), Jeffamine EDR148 (trade name), and polyamide amine is preferable in view of the surface curability.

In view of improving the storage stability and the surface curability of the composition according to the fifth aspect of the present invention by incorporating the oxazolidine compound in combination with the ketimine compound, examples of the preferable ketimine compounds among the ketimine compounds having a bulky substituent near the ketimine bond are: ketimines produced from methyl isopropyl ketone (MIPK) or methyl t-butyl ketone (MTBK) and Jeffamine EDR148 (trade name, a dimethyleneamine having polyether skeleton); ketimines produced from MIPK or MTBK and 1,3BAC; ketimines produced from MIPK or MTBK and dimethyleneamine having norbornane skeleton (trade name, NBDA); ketimines produced from MIPK or MTBK and MXDA; ketimines produced from MIPK or MTBK and polyamide amine (trade name, X2000); ketimines produced from MIPK or MTBK and menthene diamine; and ketimines produced from MIPK or MTBK and metaphenylene diamine.

Among these, use of the ketimine produced from MIPK or MTBK and NBDA, and the ketimine produced from MIPK and 1,3BAC results in the improved surface curability of the resulting composition. Use of the ketimine produced from MIPK or MTBK and X2000 results in the improved adhesion to wet surface of the resulting composition.

The ketimine compound used in the fifth aspect of the present invention can be synthesized by the method which is the same as the one used for synthesizing the ketimine compound used in the composition according to the second aspect of the present invention.

In the composition according to the fifth aspect of the present invention, the ketimine compound is used at an amount such that the molar ratio of [epoxy group/imino group in the ketimine compound] is in the range of 0.5 to 5, and preferably 1 to 3. When the molar ratio is within such range, the resulting composition according to the fifth aspect of the present invention will enjoy improved surface curability with its storage stability and depth curability retained at a sufficient level.

It should be noted that, in the fifth aspect of the present invention, an aldimine synthesized from an aldehyde compound and an amine which is a compound corresponding to the ketimine compound as described above is also included within the ketimine compound of the present invention for the sake of convenience.

In addition to the polyepoxy compound, the oxazolidine compound represented by the formula (16), and the optional ketimine compound, the composition according to the fifth aspect of the present invention may also contain other additives such as a curing accelerator, a silane coupling agent, calcium carbonate, a filler, a plasticizer, a thixotropic agent, a pigment, a dye, an antiaging agent, an antioxidant, an antistat, a flame retardant, a tackifier, a dispersant, and a solvent at an amount which does not detract from the objects of the present invention.

The curing accelerator, silane coupling agent, calcium carbonate, and other additives used may be the same as those described in the sections of "[1]<Curing accelerator >, <Silane coupling agent>, <Calcium carbonate>, and <Other additives>".

The method for producing the composition according to the fifth aspect of the present invention is not particularly limited. The composition is typically produced by thoroughly kneading and uniformly dispersing the polyepoxy compound and the oxazolidine compound represented by the formula (16), and preferably, the ketimine compound, and optional other additives as described above in a mixer or other agitating means under reduced pressure or in an inert atmosphere such as nitrogen.

The moisture-curable epoxy resin composition according to the fifth aspect of the present invention constituted as described above contains the oxazolidine compound of particular type for the latent curing agent, and consequently, it exhibits excellent surface and depth curability as well as sufficient storage stability.

The composition according to the fifth aspect of the present invention containing the oxazolidine compound represented by the formula (16) wherein $R^{17}$ bonded to the ring member nitrogen is methyl group or ethyl group exhibits particularly excellent surface curability since the oxazolidine compound undergoes immediate hydrolysis.

The composition according to the fifth aspect of the present invention containing the oxazolidine compound represented by the formula (16) wherein $R^{18}$ bonded to the ring member carbon is a branched carbon or a ring member carbon exhibits particularly excellent storage stability.

The composition according to the fifth aspect of the present invention containing a ketimine compound also exhibits excellent surface curability.

The composition according to the fifth aspect of the present invention containing a ketimine compound which has a bulky substituent near its ketimine bond exhibits particularly excellent surface curability and storage stability.

Therefore, the composition according to the fifth aspect of the present invention is well adapted for use in an adhesive, sealant, potting agent, coating composition and the like.

Although the composition according to the fifth aspect of the present invention has been described as a one-part epoxy resin composition, it should be understood that, in the use of the composition, the composition according to the fifth aspect of the present invention can also be used as a two-part epoxy resin composition.

It should be noted that, in the second, fourth, and fifth aspects of the present invention, an aldimine synthesized from an aldehyde compound and an amine which is a compound corresponding to the ketimine compound as described above is also included within the ketimine compound for the sake of convenience.

An aldimine is a compound which is produced through a reaction between a polyamine and an aldehyde. The polyamine may be the same as those described above.

Exemplary aldehydes are aliphatic aldehydes such as acetaldehyde, 2-methylbutyl aldehyde, propione aldehyde, and n-butyl aldehyde; and aromatic aldehydes such as benzaldehyde, trimethylbenzaldehyde, and methoxybenzaldehyde.

The ketimine compound of the present invention as described above, or the ketimine compound and the aldimine as described above, may be used either alone or as a mixture of two or more such compounds. However, use of a ketimine compound is preferable in view of the relatively mild reaction.

EXAMPLES

Next, the present invention according to the first to fifth aspects of the invention is described in further detail. It should be understood that the embodiments of the present invention according to the first to fifth aspects of the invention are not limited to those described below.

Examples 1–1 to 1–3 and Comparative Examples 1–1 to 1–2

The starting materials as described below were used in the amounts shown in Table 1 to produce the moisture-curable epoxy resin composition shown in Table 1.

The thus prepared moisture-curable epoxy resin compositions were determined for their depth curability, surface curing time, and storage stability by the procedure as described below.

TABLE 1

(unit: parts by weight)

|  | Examples | | | Comparative Examples | |
|---|---|---|---|---|---|
|  | 1-1 | 1-2 | 1-3 | 1-1 | 1-2 |
| Universal epoxy resin | 100 | — | — | — | — |
| OH-free epoxy resin | — | 100 | 100 | 100 | 100 |
| Oxazolidine 1 | 40 | 40 | 20 | — | — |
| Oxazolidine 2 | — | — | — | — | 40 |
| Ketimine 1 | — | — | 20 | 40 | — |
| Thickness of cured film (mm) | >5 | >5 | >5 | 0.8 | >5 |
| Surface curing time (day) | 2 | 2.5 | <1 | <1 | 2.5 |
| Viscosity increase (folds) | 10 | 3 | 5 | 3 | >500 |

Universal epoxy resin: EP4100E, manufactured by Asahi Denka Kogyo K.K.
OH-free epoxy resin: DER 332, manufactured by Dow Chemical Japan, content of hydroxyl group in the skeleton: 0% by mole.
Oxazolidine 1: the compound represented by formula (5):

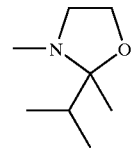

(5)

Oxazolidine 2: the compound represented by formula (6):

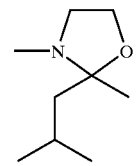

(6)

Ketimine 1: the compound represented by formula (7):

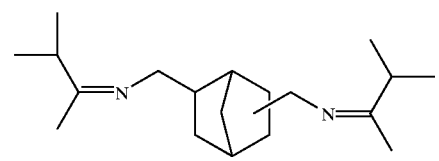

(7)

<Test of Depth Curability and Surface Curing Time>

The depth curability of the moisture-curable epoxy resin compositions as described above was evaluated by filling a polypropylene cup container having a height of 1 cm with the moisture-curable epoxy resin composition to its full height, and leaving the composition in an environment at a temperature of 20° C. and relative humidity of 55% for 7 days. Surface curing time was determined in terms of the tack-free time of the cured film surface when the composition was left. The results are shown in Table 1. Thickness of the cured film after seven days was also measured. The results are also shown in Table 1.

<Storage Stability Test>

The moisture-curable epoxy resin compositions as described above were evaluated for their storage stability by leaving the composition in a sealed container at 70° C. for 1 day. Increase in viscosity of the composition after one day was calculated by assuming the viscosity of the composition immediately after its preparation as 1. The results are shown in Table 1.

As shown in Table 1, Comparative Example 1—1 containing ketimine 1 as the only latent curing agent exhibited good storage stability while the depth curability, and hence, the film thickness were insufficient. Comparative Example 1–2 containing as the latent curing agent oxazolidine 2 wherein nitrogen atom in the heterocyclic ring is not very much sterically hindered exhibited good depth curability while the storage stability was very poor.

On the other hand, Examples 1–1 to 1–3 containing the oxazolidine compound according to the first aspect of the present invention exhibited excellent depth curability, and the cured film had a thickness as much as 5 mm after 1 week. Examples 1–1 to 1–3 also exhibited storage stability better than Comparative Example 1–2 containing an oxazolidine compound of weak steric hindrance. The very low viscosity increase of Example 1–2 indicates that the storage stability can be further improved by using a polyepoxy compound having a OH group content in its skeleton of up to 10% by mole. Example 1–3 demonstrates that surface curing speed can be accelerated, and also, storage stability can be improved without detracting from the depth curability by using the oxazolidine compound according to the first aspect of the present invention in combination with ketimine 1.

Examples 2–1 to 2–3 and Comparative Examples 2–1 to 2—2

The starting components were mixed at the mixing ratio shown in Table 2 to produce the moisture-curable epoxy resin compositions.

The thus prepared moisture-curable epoxy resin compositions were determined for their surface curing time and storage stability by the procedure as described below.

TABLE 2

|  | Examples | | |
|---|---|---|---|
|  | 2-1 | 2-2 | 2-3 |
| Epoxy resin | 100 | 100 | 100 |
| Oxazolidine 1 | 40 | 40 | 20 |
| Ketimine 1 |  |  | 20 |
| Silyl phosphate ester | 1 |  | 0.5 |
| Acidic phosphoric acid |  | 1 |  |
| Thickness of cured film (mm) | >5 1.5 | >5 1.5 | >5 <1 |

TABLE 2-continued

|  | Examples | | |
|---|---|---|---|
|  | 2-1 | 2-2 | 2-3 |
| Surface curing time (day) | 10 | 10 | 15 |
| Viscosity increase (folds) |  |  |  |

Epoxy resin: trade name, EP4100E; manufactured by Asahi Denka Kogyo K.K.; epoxy equivalent, 190.
Oxazolidine 1: an oxazolidine compound represented by formula (5) which is the same as the one used in Examples 1-1 to 1-3.
Ketimine 1: a ketimine represented by formula (7) which is the same as the one used in Examples 1-1 to 1-3.
Silyl phosphate ester: trimethyl silyl ester of dioctyl phosphate represented by formula (14):

(14)

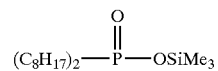

Acidic phosphoric acid: dioctyl phosphate represented by formula (15):

(15)

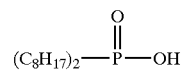

<Surface Curing Time>

A polypropylene cup having a diameter of about 3 cm and a height of 5 mm was filled with the moisture-curable epoxy resin compositions produced in Examples 2–1 to 2–3 and Comparative Examples 2–1 to 2—2 to its full height, and the composition was left in an environment at a temperature of 20° C. and relative humidity of 55% to measure the time required until no tack was observed when a polyethylene sheet was brought in contact with the resin composition.

<Storage Stability Test>

The moisture-curable resin compositions as described above were evaluated for their initial viscosity and the viscosity after leaving under viscosity-increasing conditions (70° C.) for 1 day by using B-type viscometer. Increase in the viscosity was calculated by dividing the viscosity after leaving under viscosity-increasing conditions by the initial viscosity. The results are shown in Table 2.

Examples 3–1 to 3–4 and Comparative Example 3-1

The compounds shown in Table 3 were mixed at the amount shown in Table 3 to produce the moisture-curable epoxy resin compositions as shown in Table 3. The thus prepared compositions were determined for their surface curing time and storage stability by the procedure as described below.

It should be noted that the compositions produced in Examples 3–1 to 3–4 and Comparative Example 3-1 were excellent in depth curability when the depth curability of the compositions was evaluated by filling a polypropylene cup container having a height of 1 cm with the composition to its full height, and leaving the composition in an environment at a temperature of 20° C. and relative humidity of 60% for 7 days to measure thickness of the cured film. The thickness of the cured film was 5 mm or thicker for all compositions indicating the satisfactory depth curability.

TABLE 3

(unit: parts by weight)

|  | Examples | | | | Comp. Example |
| --- | --- | --- | --- | --- | --- |
|  | 3-1 | 3-2 | 3-3 | 3-4 | 3-1 |
| Epoxy resin | 100 | 100 | 100 | 100 | 100 |
| Oxazolidine A | 35 | — | — | 25 | — |
| Oxazolidine B | — | 35 | — | — | — |
| Oxazolidine C | — | — | 35 | — | — |
| Oxazolidine D | — | — | — | — | 35 |
| Ketimine 1 | — | — | — | 10 | — |
| Surface curability (Surface curing time) | 18 hr. | 15 hr. | 15 hr. | 12 hr. | 5 days |
| Storage stability (viscosity increase) | 10 folds | — | — | — | 500 folds |

Epoxy resin: EP4100E manufactured by Asahi Denka Kogyo K.K.
Oxazolidine A: the compound represented by formula (17).
Oxazolidine B: the compound represented by formula (18).
Oxazolidine C: the compound represented by formula (19).
Oxazolidine D: the compound represented by formula (20):

(20)

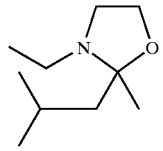

Ketimine 1: the ketimine represented by formula (7) which is the same as the one employed in Examples 1-1 to 1-3.

<Surface Curing Time>

The surface curing time was measured by filling a polypropylene cup container having a height of 1 cm with the moisture-curable epoxy resin composition to its full height, and leaving the composition in an environment at a temperature of 20° C. and relative humidity of 60%. Surface curing time was determined in terms of the tack-free time of the cured film surface when the composition was left. The results are shown in Table 3.

<Storage Stability Test>

The moisture-curable epoxy resin compositions as described above were evaluated for their viscosity increase after one day by assuming the viscosity of the moisture-curable epoxy resin composition immediately after the preparation as 1 by the procedure similar to <Storage stability test>in Examples 1–1 to 1–3. The results are shown in Table 3.

The present invention has been described above by referring to the oxazolidine compound according to the first aspect of the present invention, the moisture-curable epoxy resin composition according to the second aspect of the present invention, the latent curing agent according to the third aspect of the present invention, the moisture-curable epoxy resin composition according to the fourth aspect of the present invention, and the moisture-curable epoxy resin composition according to the fifth aspect of the present invention. The present invention is not limited to the Examples as described above, and it is to be understood that various modifications and variations may be made thereto in the light of the above teachings within the scope of the invention.

What is claimed is:

1. A moisture-curable epoxy resin composition comprising a polyepoxy compound having two or more epoxy groups in the molecule, and the oxazolidine compound represented by:

wherein $R^1$ is methyl group or ethyl group:

$R^2$ is an alkyl group containing 1 to 6 carbon atoms;

$R^3$ is methyl group or ethyl group;

$R^4$ is hydrogen atom, methyl group or ethyl group;

$R^5$ is a hydrogen atom or a hydrocarbon group containing 1 to 6 carbon atoms;

with the proviso that $R^2$, $R^3$ and $R^4$ may together represent an alicyclic ring or an aromatic ring; and that $R^3$ and $R^5$ may together represent an alicyclic ring or an aromatic ring.

2. A moisture-curable epoxy resin according to claim 1 wherein the skeleton of said polyepoxy compound contains up to 10% by mole of hydroxyl group.

3. A moisture-curable epoxy resin composition comprising a polyepoxy compound having two or more epoxy groups in the molecule, and an oxazolidine compound represented by:

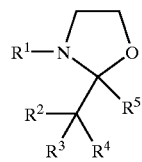

wherein $R^1$ is a methyl group:

$R^2$ is an alkyl group containing 1 to 6 carbon atoms;

$R^3$ is methyl group or ethyl group;

$R^4$ is hydrogen atom, methyl group or ethyl group;

$R^5$ is hydrogen atom or a hydrocarbon group containing 1 to 6 carbon atoms;

with the proviso that $R^2$, $R^3$ and $R^4$ may together represent an alicyclic ring or an aromatic ring; and that $R^3$ and $R^5$ may together represent an alicyclic ring or an aromatic ring.

4. A moisture-curable epoxy resin composition according to claim 1 wherein the skeleton of said polyepoxy compound contains up to 10% by mole of hydroxyl group.

* * * * *